United States Patent
Ho et al.

(10) Patent No.: US 9,212,772 B2
(45) Date of Patent: Dec. 15, 2015

(54) NEEDLE FREE CONNECTOR

(71) Applicant: Pacific Hospital Supply Co., Ltd, Taipei (TW)

(72) Inventors: Shih-Chi Ho, Taipei (TW); Ming-Chung Chen, Taipei (TW)

(73) Assignee: PACIFIC HOSPITAL SUPPLY CO., LTD, Taipei (TW)

( * ) Notice: Subject to any disclaimer, the term of this patent is extended or adjusted under 35 U.S.C. 154(b) by 337 days.

(21) Appl. No.: 13/840,573

(22) Filed: Mar. 15, 2013

(65) Prior Publication Data

US 2014/0265318 A1    Sep. 18, 2014

(51) Int. Cl.
*F16L 37/08* (2006.01)
*A61M 39/00* (2006.01)

(52) U.S. Cl.
CPC ............... *F16L 37/08* (2013.01); *A61M 39/00* (2013.01)

(58) Field of Classification Search
CPC .................... A61M 2039/1027; A61M 39/26; A61M 2039/268
USPC .................................. 604/905, 249, 256, 536
See application file for complete search history.

(56) References Cited

U.S. PATENT DOCUMENTS

| | | | | |
|---|---|---|---|---|
| 3,806,086 | A * | 4/1974 | Cloyd | 604/249 |
| 5,242,393 | A * | 9/1993 | Brimhall et al. | 604/249 |
| 5,353,837 | A * | 10/1994 | Faust | 604/249 |
| 5,439,451 | A * | 8/1995 | Collinson et al. | 604/256 |
| 5,749,861 | A * | 5/1998 | Guala et al. | 604/249 |
| 6,228,069 | B1 * | 5/2001 | Barth et al. | 604/249 |
| 6,595,981 | B2 * | 7/2003 | Huet | 604/523 |
| 6,755,391 | B2 * | 6/2004 | Newton et al. | 604/249 |
| 6,883,778 | B1 * | 4/2005 | Newton et al. | 604/256 |
| 6,991,215 | B2 * | 1/2006 | Kiehne | 604/249 |
| 7,753,892 | B2 * | 7/2010 | Newton et al. | 604/246 |
| 7,789,864 | B2 * | 9/2010 | Cote et al. | 604/256 |
| 7,837,658 | B2 * | 11/2010 | Cote et al. | 604/236 |
| 7,998,134 | B2 * | 8/2011 | Fangrow et al. | 604/535 |
| 8,182,452 | B2 * | 5/2012 | Mansour et al. | 604/256 |
| 8,414,542 | B2 * | 4/2013 | Stroup | 604/246 |
| 8,951,230 | B2 * | 2/2015 | Tanabe et al. | 604/249 |

* cited by examiner

*Primary Examiner* — David E Bochna
(74) *Attorney, Agent, or Firm* — Chun-Ming Shih

(57) ABSTRACT

A needle free connector includes a tube device having a first tube, a first locking elements formed on a distal end of the first tube and having a transverse channel in communication with the first tube and a push rod integrally formed on a side face of the first locking elements, a resilient frame securely engaged with the first locking elements and having a second ring movably positioned due to movement of the first tube and provided with a hole defined in a bottom face of the second ring to allow the first tube to movably extend therethrough, a hollow casing provided with a second tube to movably receive therein the first tube and a cap securely connected to the hollow casing to form a watertight connection.

13 Claims, 6 Drawing Sheets

NEEDLE FREE CONNECTOR

BACKGROUND OF THE INVENTION

1. Field of the Invention

This invention is related to a needle free connector, and more particular, to a connector providing a fluid path communication between a syringe and an IV (intravenous) fluid line to allow liquid originally contained in the syringe to smoothly flow into the IV fluid line.

2. Description of Related Art

Conventionally, to administer fluids or medications into patients, a syringe with sharp needle is necessarily used. However, during the processes of filling and administration, the medical staff is taking a great deal of risk of needle-stick injury. In order to avoid being hurt by the needle, numerous designs of needle free connectors are developed to meet the need. However, each one of the newly developed design is either complex in structure or expensive in price. Above all, they are not convenient when it comes to use of the same.

SUMMARY OF THE INVENTION

The primary objective of the present invention is to provide a connector used to construct a fluid path between a syringe and an IV fluid line to smoothly and readily transfer fluid or medication originally contained in the syringe to the IV fluid line.

Another objective of the present invention is to provide a resilient frame installed in the connector to automatically reseal the fluid path in a watertight manner after the syringe or equivalent is removed.

In order to accomplish the aforementioned objective, the needle free connector constructed in accordance with the present invention is composed of a tube device having a first hollow tube, first locking elements integrally formed with the first tube and provided with a first ring formed on an outer periphery of the first locking elements, a transverse channel defined in the first ring and the first locking elements to communicate with the first tube, a push rod integrally extending from a side of the first ring in a direction opposite to that of the first tube and a mark formed on a distal free end of the push rod;

a resilient frame having a second ring to securely engage with the first locking elements of the tube device, a hole defined in a bottom face of the second ring and adapted to accommodate therethrough the first tube of the tube device, second locking elements extruded from a side of the second ring to correspond to the first locking elements of the tube device, a neck extending from the second locking elements and a third ring integrally formed on a distal free edge of the neck and having third locking elements formed on an inner face of the third ring;

a hollow casing having a second hollow tube integrally extending out of the casing, a first positioning element formed on an inner face of the hollow casing and a second positioning element formed on a distal end of the hollow casing; and a flared cap securely and sealingly connected to the hollow casing to form a watertight connection.

BRIEF DESCRIPTION OF THE DRAWINGS

The invention, as well as its many advantages, may be further understood by the following detailed description and accompanying drawings.

DETAILED DESCRIPTION OF THE INVENTION

Figure 1:
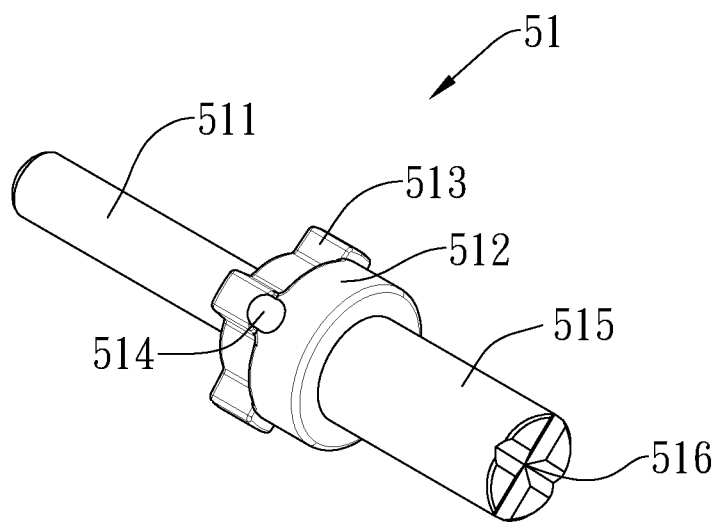
FIG. 1 is a perspective view of the tube device constructed in accordance with the present invention.
Figure 4:
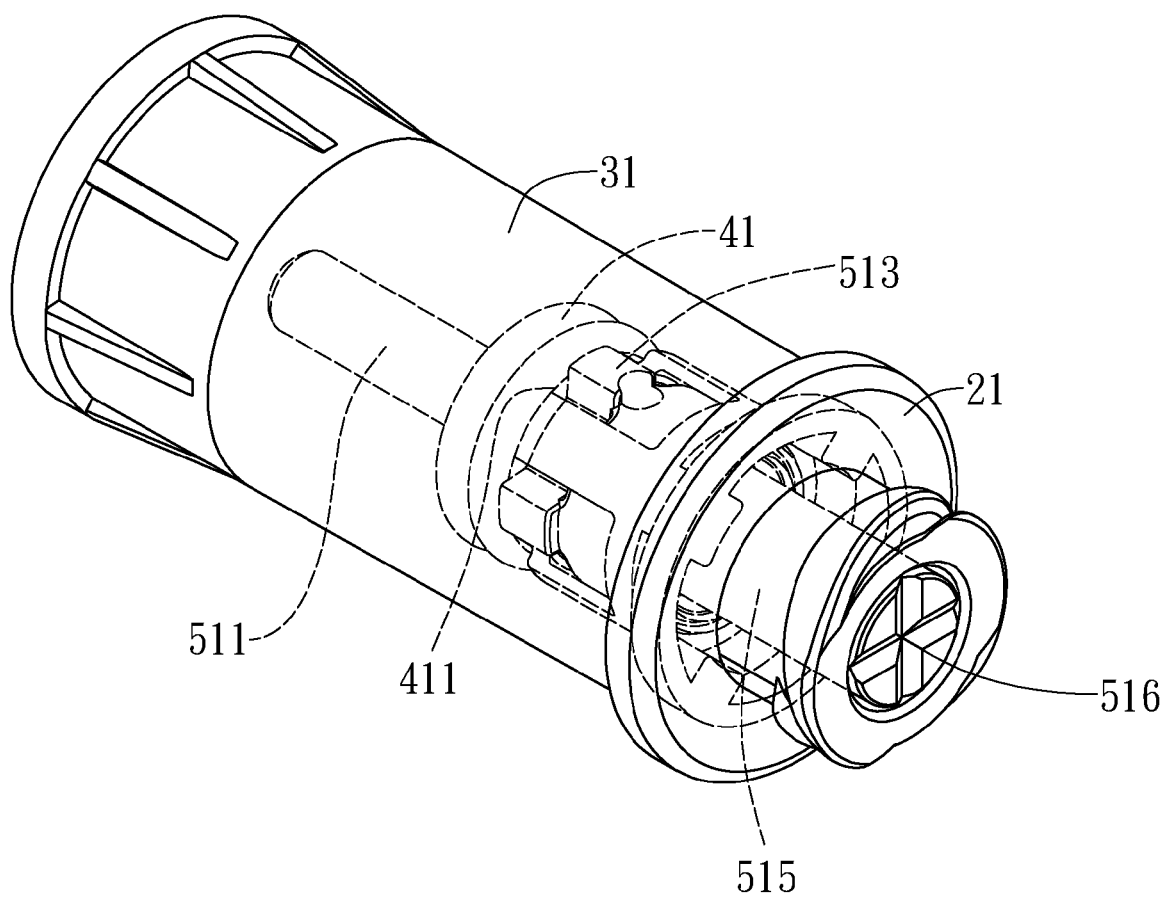
FIG. 4 is a perspective view showing the assembly of the needle free connector in accordance with present invention.

With reference to FIGS. 1 and 4, it is to be noted that the needle free connector constructed in accordance with the preferred embodiment of the present invention has a tube device 51, a resilient frame 41, a casing 31, and a flared cap 21.

With reference to FIG. 1, the tube device 51 has a first hollow tube 511, first locking elements 513 integrally formed with the first tube 511 and provided with a first ring 512 formed on an outer periphery of the first locking elements 513, a transverse channel 514 defined in the first ring 512 and the first locking elements 513 to communicate with the first tube 511, a push rod 515 integrally extending from a side of the first ring 512 in a direction opposite to that of the first tube 511 and a mark 516 formed on a distal free end of the push rod 515.

Figure 2:
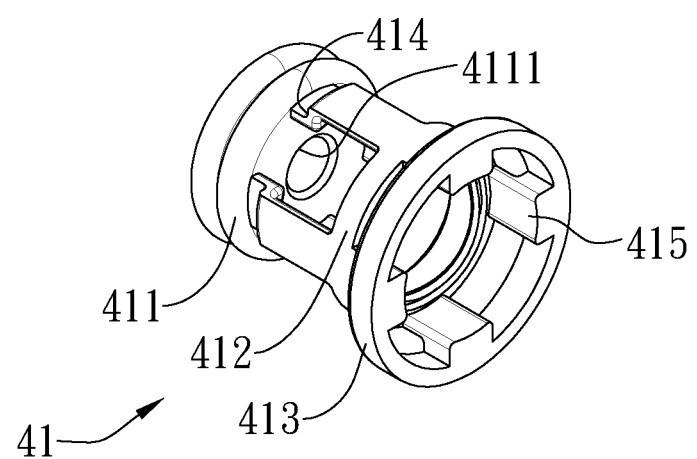
FIG. 2 is a perspective view of the resilient frame constructed in accordance with the present invention.

With reference to FIG. 2, the resilient frame 41 has a second ring 411 to securely engage with the first locking elements 513 of the tube device 51, a hole 4111 defined in a bottom face of the second ring 411 and adapted to accommodate therethrough the first tube 511 of the tube device 51, second locking elements 414 extruded from a side of the second ring 411 to correspond to the first locking elements 513 of the tube device 51, a neck 412 extending from the second locking elements 414 and a third ring 413 integrally formed on a distal free edge of the neck 412 and having third locking elements 415 formed on an inner face of the third ring 413.

Figure 3:
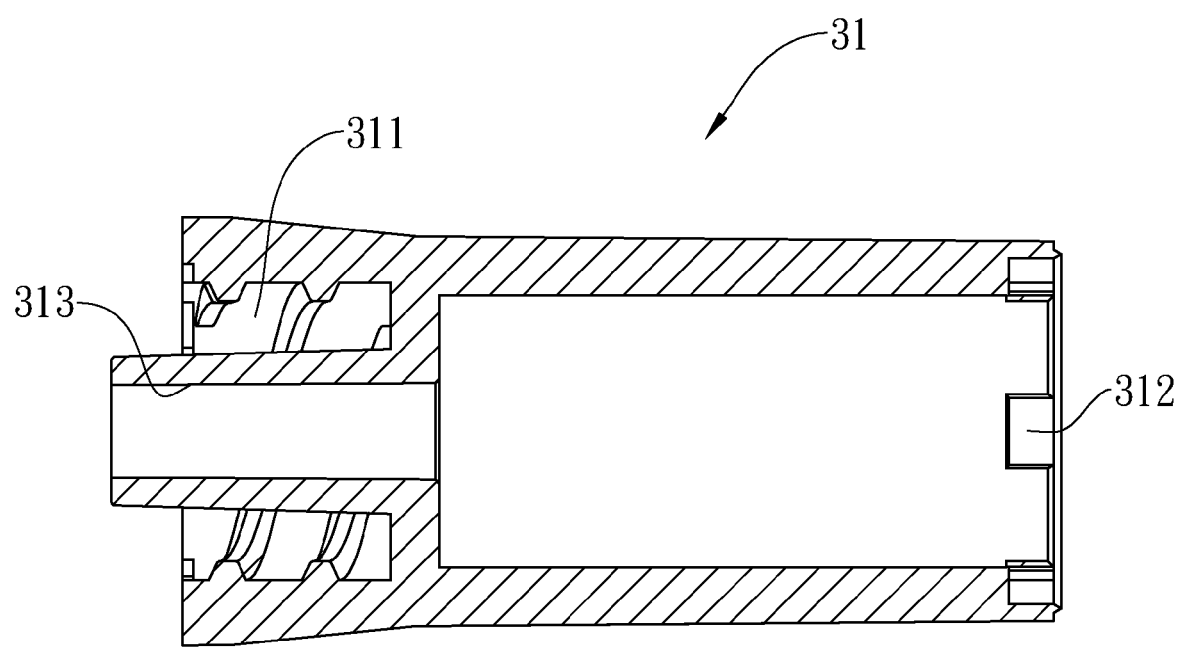
FIG. 3 is a cross sectional view of the hollow casing constructed in accordance with the present invention.

With reference to FIG. 3, the hollow casing 31 has a second hollow tube 313 integrally extending out of the casing 31 to receive therein the first tube 511 of the tube device 51, a first positioning element 311 formed on an inner face of the hollow casing 31 and a second positioning element 312 formed on a distal end of the hollow casing 31. Preferably, the first positioning element 311 is a thread.

As shown in FIG. 4, the flared cap 21 with a centrally defined through hole therethrough is securely and sealingly connected to the hollow casing 31 in a watertight manner via the assistance of the second positioning element 312 of the hollow casing 31 and the third ring 413 of the resilient frame 41, and the outer face of the cap 21 is threaded for better connection with syringe, more particularly, luer-lock syringe.

It is to be noted from the depiction of FIG. 4 that after the needle free connector of the preferred embodiment of the present invention is assembled, the first tube 511 extends through the hole 4111 of the resilient frame 41 to allow the first locking elements 513 to securely connect to the second ring 411. In the meantime, the first locking elements 513 is fitted into the second locking elements 414 of the resilient frame 41 to fix the tube device 51 inside the resilient frame 41. It may be understood that the first locking elements 513 of the tube device 51 may be protruded out of the first ring 512 or the first locking elements 513 may be recessed inside the first ring 512. Contrast to the structure of the first locking elements 513, the second locking elements 414 may be recessed in the second ring 411 to receive therein the protruded first locking elements 513 or the second locking elements 414 may be protruded out of the second ring 411 to be received inside the recessed first locking elements 513.

After the assembly between the tube device 51 and the resilient frame 41, the first tube 511 extends through the second hollow tube 313 of the hollow casing 31. After which, the flared cap 21 is securely connected to a peripheral edge of the hollow casing 31 via such as supersonic welding and the third ring 413 of the resilient frame 41 is closely combined to the first ring 512 of the tube device 51 in a watertight manner. Furthermore, the mark 516 formed on the distal end of the push rod 515 may be a protruded mark or a recessed mark to function as a guidance for fluid flowing thereby.

Figure 5:
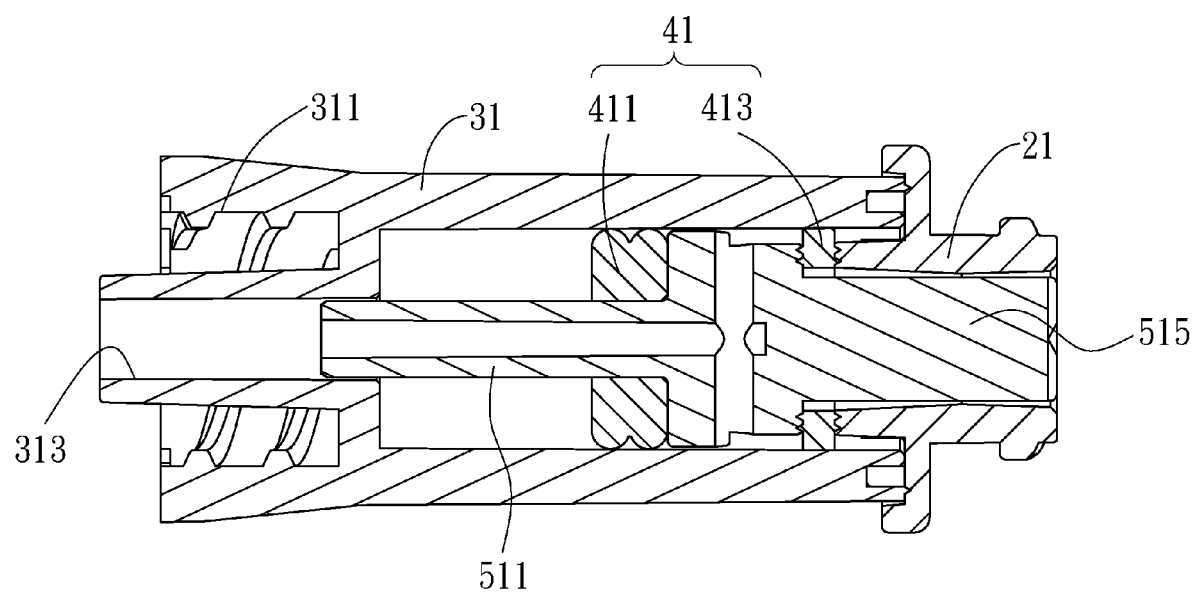
FIG. 5 is a cross sectional view showing the relative position of the elements after assembly.
Figure 5A:
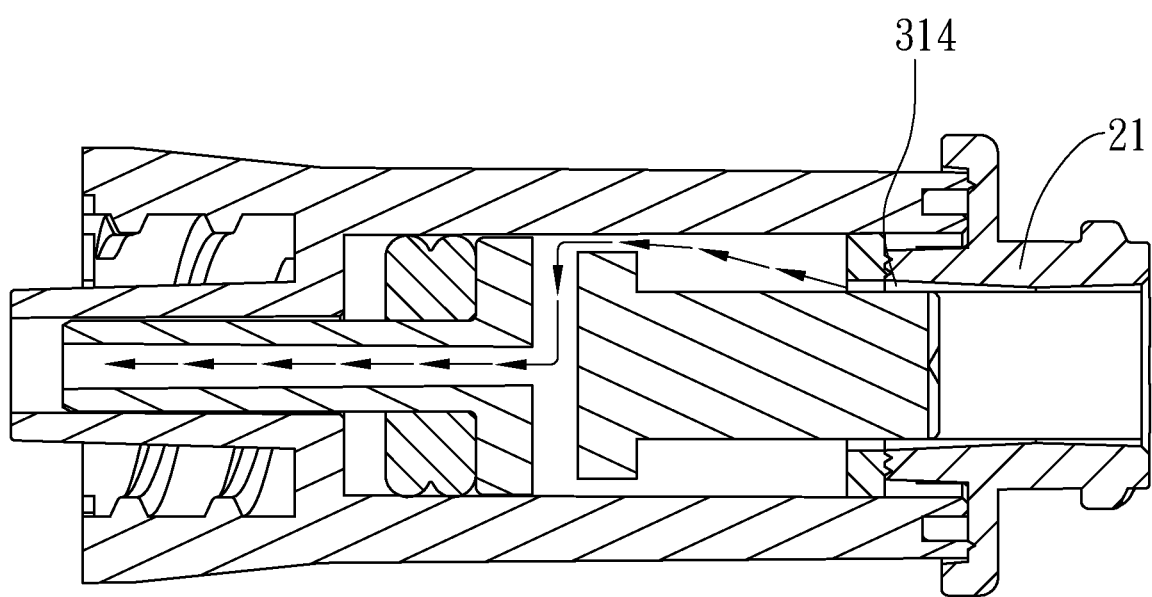
FIG. 5A is a cross sectional view showing the connector in a working position of the present invention.

With reference to FIGS. 5 and 5A, when the needle free connector of the preferred embodiment of the present invention is used, the push rod 515 of the tube device 51 is provided for connection with a syringe or equivalent and the first positioning element 311 of the hollow casing 31 is to connect to another object, such as an IV (intravenous) fluid line (not shown). After the pointed head of the syringe is engaged with the distal free end of the push rod 515, a force is exerted upon the push rod 515 to force the tube device 51 to move relative to the hollow casing 31. Due to the resilience of the material used for the resilient frame 41, the resilient frame 41 together with the tube device 51 is moved inside the hollow casing 31 to define a path 314 between the outer sidewall of the first ring 512 and an inner sidewall of the third ring 413. With the provision of the path 314, fluid inside the syringe is able to be administered to flow through the mark 516 first so that the fluid is guided to flow along the push rod 515. When the fluid is flowing along the push rod 515 and because of the provision of the transverse channel 514 defined in the first ring 512 and first locking elements 513 and in communication with the first tube 511, the fluid is able to flow through the transverse channel 514 and into the first tube 511. Eventually, the fluid flows to, such as, the IV fluid line.

After the fluid transfer is successfully completed, the force originally exerted on the push rod 515 is removed. Thus, the tube device 51 as well as the resilient frame 41 returns to its original position.

During the entire fluid transfer, there is no requirement of any needle so that the medical staff takes no potential risk of needle-stick injuries.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A needle free connector comprising:
a tube device having a first tube, first locking elements formed on a distal end of the first tube and having a first ring formed on an outer periphery thereof, a transverse channel provided between the first locking elements and the first ring and being in communication with the first tube, and a push rod integrally formed on a side face of the first locking elements and extending in a direction opposite to that of the first tube;
a resilient frame securely engaged with the first locking elements and having a second ring movably positioned between a first position and a second position due to movement of the first tube and provided with a hole defined in a bottom face of the second ring to allow the first tube to movably extend therethrough, second locking elements extending from the second ring and a third ring formed on a distal end of the second locking elements;
a hollow casing provided with a second hollow tube to movably receive therein the first tube; and
a cap securely connected to the hollow casing to form a watertight connection,
wherein the first ring is disposed inside the resilient frame and is slidable against the third ring.

2. The connector as claimed in claim 1, wherein the resilient frame has a neck extruded from a side of the second locking elements to correspond to the first ring.

3. The connector as claimed in claim 2, wherein the hollow casing has a first positioning element formed on an inner face of the hollow casing for connection to a first object and a second positioning element formed oppositely to the first positioning element for connection to a second object.

4. The connector as claimed in claim 3, wherein the cap is sealingly connected to the hollow casing via the second positioning element of the hollow casing.

5. The connector as claimed in claim 4, wherein the first positioning element is a thread, and the outer face of the cap is threaded.

6. The connector as claimed in claim 3, wherein the first positioning element is a thread, and the outer face of the cap is threaded.

7. The connector as claimed in claim 3, wherein a third locking element is formed on an inner face of the third ring to engage with the second positioning element of the hollow casing.

8. The connector as claimed in claim 1, wherein the hollow casing has a first positioning element formed on an inner face of the hollow casing for connection to a first object and a second positioning element formed oppositely to the first positioning element for connection to a second object.

9. The connector as claimed in claim 8, wherein the cap is sealingly connected to the hollow casing via the second positioning element of the hollow casing.

10. The connector as claimed in claim 9, wherein the first positioning element is a thread, and the outer face of the cap is threaded.

11. The connector as claimed in claim 8, wherein the first positioning element is a thread, and the outer face of the cap is threaded.

12. The connector as claimed in claim 8, wherein a third locking element is formed on an inner face of the third ring to engage with the second positioning element of the hollow casing.

13. The connector as claimed in claim 1, wherein the push rod is formed a mark on a distal free end thereof.

* * * * *